United States Patent [19]

Ilvespää et al.

[11] 4,130,652
[45] Dec. 19, 1978

[54] 2-(IMINOETHYLIDENE)-PYRROLIDINES AND TAUTOMERIC 2-(AMINOETHENYL)-1-PYRROLINES

[75] Inventors: Atso Ilvespää, Allschwil; Walter Fuhrer, Frenkendorf, both of Switzerland

[73] Assignee: Ciba-Geigy Corporation, Ardsley, N.Y.

[21] Appl. No.: 771,294

[22] Filed: Feb. 23, 1977

[30] Foreign Application Priority Data

Feb. 27, 1976 [CH] Switzerland ............... 2441/76

[51] Int. Cl.$^2$ ............... A61K 31/40; C09B 23/00
[52] U.S. Cl. ............... 424/274; 260/326.5 J; 260/326.85; 260/326.9; 424/315; 424/316; 542/422; 542/423; 542/455; 542/457
[58] Field of Search ............... 542/422, 423, 455, 457; 260/326.5 J, 326.85, 326.9; 424/274, 315, 316

[56] References Cited

U.S. PATENT DOCUMENTS

| | | | |
|---|---|---|---|
| 3,786,047 | 1/1974 | Kuhlthau | 542/423 |
| 3,840,524 | 10/1974 | Grisar et al. | 260/326.85 X |
| 3,873,530 | 3/1975 | Viehe et al. | 260/326.85 X |

FOREIGN PATENT DOCUMENTS 1520992 4/1968 France.

*Primary Examiner*—Thomas A. Waltz
*Attorney, Agent, or Firm*—John J. Maitner

[57] ABSTRACT

The present invention provides new imino compounds having the formula I

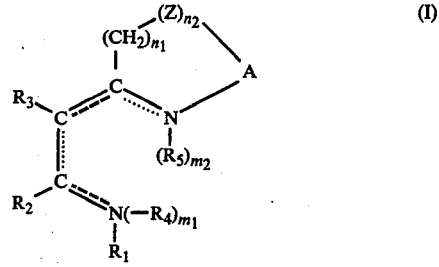

wherein
  $R_1$ represents an aliphatic or cycloaliphatic hydrocarbon radical, unsubstituted or substituted phenyl, or phenyl-lower alkyl or diphenyl-lower alkyl, which radicals are unsubstituted or substituted in the phenyl ring(s),
  $R_2$ represents unsubstituted or substituted phenyl, unsubstituted or substituted monocyclic heteroaryl or lower alkyl,
  $R_3$ represents hydrogen, lower alkyl, a carbonyl group linked with $R_2$ to form a five-membered ring, or the group $R_6$—CO wherein $R_6$ represents lower alkyl or unsubstituted or substituted phenyl,
  $R_4$ represents, if present, hydrogen or lower alkyl which is independent or is linked with $R_1$ to form a five- to seven-membered ring which can contain as ring members two aromatic ring carbon atoms of an unsubstituted or substituted phenyl or phenyl-lower-alkyl radical $R_1$, and as a six- or seven-membered ring also epoxy or lower alkylimino which is separated by two, or at least two, carbon atoms from the nitrogen atom given in the formula I,
  $R_5$ represents, if present, hydrogen or lower alkyl,
  A represents a straight- or branched-chain lower alkylene having 2 to (5-$n_1$-$n_2$) chain members,
  Z represents epoxy, epithio, imino or lower alkylimino, and
  $m_1$ and $m_2$ represent 0 or 1 and together always represent 1,
  $n_1$ represents 1 or, if Z represents imino or lower alkylimino and $n_2$ represents 1, can also represent 0,
  $n_2$ represents 0 or 1,
and wherein two additional bonds, either corresponding to the dashed lines or corresponding to the dotted lines, are present, with $m_1$ representing 0 in the former case and $m_2$ representing 0 in the latter case, and the acid addition salts, in particular the pharmaceutically acceptable acid addition salts thereof. These new substances possess valuable pharmacological properties, particularly hypoglycaemic activity.

15 Claims, No Drawings

2-(IMINOETHYLIDENE)-PYRROLIDINES AND TAUTOMERIC 2-(AMINOETHENYL)-1-PYRROLINES

DETAILED DESCRIPTION

The present invention relates to new imino compounds and to their acid addition salts, to pharmaceutical compositions which contain these new substances and to a method for the oral treatment of hyperglycaemia.

The new imino compounds according to the invention correspond to the formula I

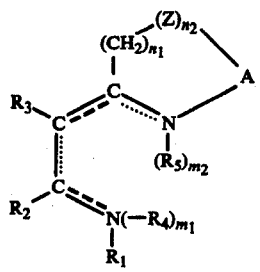

wherein
- $R_1$ represents an aliphatic or cycloaliphatic hydrocarbon radical, unsubstituted or substituted phenyl, or phenyl-lower alkyl or diphenyl-lower alkyl, which radicals are unsubstituted or substituted in the phenyl ring(s),
- $R_2$ represents unsubstituted or substituted phenyl, unsubstituted or substituted monocyclic heteroaryl or lower alkyl,
- $R_3$ represents hydrogen, lower alkyl, a carbonyl group linked with $R_2$ to form a five-membered ring, or the group $R_6$—CO wherein $R_6$ represents lower alkyl or unsubstituted or substituted phenyl,
- $R_4$ represents, if present, hydrogen or lower alkyl which is independent or is linked with $R_1$ to form a five- to seven-membered ring which can contain as ring members two aromatic ring carbon atoms of an unsubstituted or substituted phenyl or phenyl-lower-alkyl radical $R_1$, and as a six- or seven-membered ring also epoxy or lower alkylimino which is separated by two, or at least two, carbon atoms from the nitrogen atom given in the formula I,
- $R_5$ represents, if present, hydrogen or lower alkyl,
- A represents a straight- or branched-chain lower alkylene having 2 to (5-$n_1$-$n_2$) chain members,
- Z represents epoxy, epithio, imino or lower alkylimino, and
- $m_1$ and $m_2$ represent 0 or 1 and together always represent 1,
- $n_1$ represents 1 or, if Z represents imino or lower alkylimino and $n_2$ represents 1, can also represent 0,
- $n_2$ represents 0 or 1, and wherein two additional bonds, either corresponding to the dashed lines or corresponding to the dotted lines, are present, with $m_1$ representing 0 in the former case and $m_2$ representing 0 in the latter case.

By lower radicals are meant, in the foregoing and in the following, radicals having a maximum of 7 carbon atoms and preferably a maximum of 4.

The subject matter of the invention embraces also the acid addition salts, particularly the pharmaceutically acceptable acid addition salts, of the compounds of the formula I, as well as the production of these acid addition salts.

In the compounds of the general formula I, $R_1$ as aliphatic or cycloaliphatic hydrocarbon radical preferably contains a maximum of 12 carbon atoms and preferably no more than one multiple bond, with this preferably not emanating from the carbon atom linked with the nitrogen atom.

Suitable aliphatic hydrocarbon radicals $R_1$ are, for example, alkyl, alkenyl and alkynyl radicals, such as methyl, ethyl, propyl, isopropyl, butyl, isobutyl, sec.-butyl, tert.-butyl, pentyl, isopentyl, 1-methylbutyl, 1-ethylpropyl, neopentyl, tert.-pentyl, hexyl, isohexyl, heptyl, isoheptyl, 1-methylhexyl, octyl, 1-methylheptyl, nonyl, decyl, undecyl, dodecyl, allyl, 2-butenyl, 2-pentenyl, 4-pentenyl, 3-methyl-2-butenyl, 2-hexenyl, 1,1-dimethyl-2-butenyl, 2,3-dimethyl-3-butenyl, 2-heptenyl, 1-methyl-3-hexenyl, 2-octenyl, 7-octenyl, 1-methyl-3-heptenyl, 1,5-dimethyl-2-hexenyl, 2-nonenyl, 8-nonenyl, 2-decenyl, 9-decenyl, 10-undecenyl, 11-dodecenyl, 2-propynyl, 1-methyl-2-propynyl, 2-butynyl, 3-butynyl, 2-pentynyl, 5-hexynyl, 1,1-dimethyl-2-butynyl or 6-heptynyl. Aliphatic hydrocarbon radicals preferably contain up to 8 carbon atoms.

By cycloaliphatic hydrocarbon radicals are meant in general radicals in which all or a part of the carbon atoms belong to one or more cycloaliphatic rings, and which contain no aromatic rings. In bi- and polycyclic radicals, adjacent cycloaliphatic rings can contain no common carbon atoms or they can contain one, two or more common carbon atoms, i.e. these radicals can be derived from compounds having two or more independent cycloalkyl rings bound directly or by way of alkylene radicals, or they can be radicals of cycloaliphatic spiro compounds, of cycloaliphatic fused (condensed) compounds or of cycloaliphatic bridge compounds, or they can contain such compounds, and in polycyclic radicals there can also be different types of ring linkages. Cycloaliphatic hydrocarbon radicals are, for example, optionally lower-alkyl-substituted cycloalkyl, cycloalkylalkyl, bicycloalkyl-lower-alkyl, cycloalkyl-cycloalkyl, spirocycloalkyl, bicycloalkyl and bicycloalkyl-lower-alkyl radicals, as well as polycycloalkyl radicals and corresponding singly unsaturated radicals, such as cyclopropyl, cyclobutyl, cyclopropylmethyl, 1-methylcyclopropyl, cyclopentyl, cyclohexyl, cycloheptyl, cyclohexylmethyl, 1-methyl-, 2-methyl-, 3-methyl- or 4-methylcyclohexyl, 2,5-dimethylcyclopentyl, cyclooctyl, 2,4-dimethyl-, 2,6-dimethyl-, 3,5-dimethyl- or 4,4-dimethylcyclohexyl, 4-ethylcyclohexyl, 4-isopropylcyclohexyl, 4-tert.-butylcyclohexyl, cis- and trans-2-cyclohexylcyclopentyl, cis- and trans-2-cyclohexylcyclohexyl, spiro[4.4]non-1-yl, spiro[4.5]dec-1-yl, spiro[4.5]dec-6-yl and spiro[4.5]dec-8-yl, spiro[5.5]undec-1-yl and spiro[5.5]undec-3-yl, hexahydroindan-1-yl and hexahydroindan-2-yl, decahydronaphthalen-1-yl, 1-norbornanyl, 2-norbornanyl, bicyclo[2,2,2]oct-2-yl, 2-norbornanylmethyl, 2-bornanyl, 1-adamantyl, cyclododecyl, 2-cyclohexenyl, 3-cyclohexenyl, 3-cycloheptyl, 1-methyl-2-cyclohexenyl, 2-methyl-2-cyclohexenyl, 2-norbornen-1-yl, 2-norbornen-7-yl and 5-norbornen-2-ylmethyl. Cycloaliphatic hydrocarbon radicals $R_1$ contain preferably up to 12 carbon atoms.

A phenyl radical $R_1$ can be substituted, for example, by halogen up to atomic number 35, particularly by chlorine, by optionally halogenated lower alkyl such as ethyl, propyl, isopropyl, butyl, tert.-butyl and especially methyl or trifluoromethyl, or by lower alkoxy or lower alkylthio such as ethoxy, propoxy, isopropoxy, butoxy, isobutoxy, ethylthio, propylthio, isopropylthio, butylthio and, in particular, methoxy or methylthio, whereby several, preferably however a maximum of three, substituents, identical or differing from each other, can be present. There can also be present as substituent, e.g., a nitro group, a di-lower-alkylamino group such as the dimethylamino group, or a lower alkanamido group such as the formamido, propionamido, butyramido and, in particular, the acetamido group. As mono- or diphenyl-loweralkyl, $R_1$ is, for example, benzyl, phenethyl, α-methylbenzyl, α-methylphenethyl, α-ethylbenzyl, 3-phenylpropyl, 4-phenylbutyl, diphenylmethyl or α-benzylbenzyl, the phenyl radicals of which can be substituted, for example, by the radicals mentioned above as substituents of phenyl radicals $R_1$.

A phenyl radical $R_2$ can carry the substituents mentioned above for $R_1$. As a monocyclic hetero aryl radical, $R_2$ is, for example, a five- to six-membered heteroaryl radical, bound by way of one of its ring carbon atoms, with an oxygen, sulphur or nitrogen atom, and optionally an additional nitrogen atom, as ring members, such as furyl, imidazolyl, oxazolyl, thiazolyl, pyridyl, pyrimidinyl or pyrazinyl and particularly thienyl. These radicals can be substituted by one or more of the radicals mentioned above as substituents of phenyl radicals $R_1$, especially by one or more of the aforementioned lower alkyl, lower alkoxy and lower alkylthio radicals, also by fluorine or chlorine. $R_2$ as lower alkyl is, for example, methyl, ethyl, propyl, isopropyl, butyl, isobutyl or tert.-butyl.

If $R_3$ represents a group $R_6$—CO—, $R_6$ as lower alkyl therein is, e.g., ethyl, propyl, isopropyl, butyl or tert.-butyl, and particularly methyl. A phenyl radical $R_6$ can carry for example the substituents given for phenyl radicals $R_1$.

A carbonyl group $R_3$, linked with $R_2$ to form a five-membered ring, forms together with $R_2$, e.g., the o-benzoylene radical.

$R_4$ is, for example, one of the lower alkyl radicals given under $R_1$. Together with the adjacent nitrogen atom, a lower alkyl $R_4$ forms, linked in the above-defined manner with an aliphatic radical $R_1$, especially with lower alkyl, for example a polymethyleneimino radical such as the 1-pyrrolidinyl, piperidino or hexahydro-1H-azepin-1-yl radical, the morpholino, 4-methyl-1-piperazinyl or 4-methylhexahydro-1H-1,4-diazepin-1-yl radical; linked with a cycloaliphatic radical $R_1$ for example the 3-azabicyclo[3.2.2]non-3-yl, 3-azabicyclo[3.3.1]non-3-yl or 1,8,8-trimethyl-3-azabicyclo[3.2.1]oct-3-yl radical; and linked with a phenyl or heteroaryl radical $R_1$ for example the 1-isoindolinyl, 1,2,3,4-tetrahydroquinolin-1-yl, 3,4-dihydro-2H-1,4-benzoxazin-4-yl of 4-methyl-1,2,3,4-tetrahydroquinoxalin-1-yl radical.

A lower alkylene A is, for example, propylene, 1,2-dimethylethylene, 2-methyltrimethylene, 1,1-dimethyltrimethylene, 2,2-dimethyltrimethylene, especially however tetramethylene or trimethylene and particularly ethylene.

As lower alkylimino, Z is for example ethylimino, propylimino, isopropylimino, butylimino, isobutylimino and especially methylimino.

The new imino compounds of the formula I and their addition salts with inorganic and organic acids possess valuable pharmacological properties, particularly hypoglycaemic activity, as can be demonstrated on rats with normal metabolism, after oral administration of doses from 10 mg/kg, as well as on rats that have been put into a diabetes-like metabolic condition by injection of streptozotocin [see A. Junod et al., Proc. Soc.Exp.Biol.Med. 126, 201-205 (1967)]. The lowering of the blood-sugar level is not accompanied by a hyperlactacidaemia. The pharmacological findings characterise the new imino compounds of the formula I and their pharmaceutically acceptable acid addition salts as antidiabetics which can be used for the oral treatment of hyperglycaemia in mammals, particularly for the oral treatment of Diabetes mellitus.

The invention relates in particular to compounds of the formula I wherein $R_1$ represents an aliphatic or cycloaliphatic hydrocarbon radical having a maximum of 12 carbon atoms, $R_2$ represents phenyl or thienyl, which radicals are unsubstituted or substituted by lower alkyl, lower alkoxy, halogen up to atomic number 35 and/or trifluoromethyl, $R_3$ represents hydrogen or lower alkyl, $R_4$, if present, represents lower alkyl, or together with $R_1$ a bivalent aliphatic or cycloaliphatic hydrocarbon radical having a minimum of 4 and a maximum of 7 carbon atoms between the two linkage points and a total of 4 to 12 carbon atoms, or the ethyleneoxyethylene radical, $R_5$, if present, represents hydrogen or lower alkyl, and A, Z, $m_1$, $m_2$, $n_1$ and $n_2$ have the meanings given under the formula I, and to their pharmaceutically acceptable acid addition salts. Of special importance are compounds of the formula I wherein $R_1$, $R_2$, $R_3$, $R_4$ and $R_5$ have the meanings just defined and $m_1$ and $m_2$ have the meanings given under the formula I, $n_1$ represents 1 and $n_2$ represents 0 and simultaneously A represents ethylene, trimethylene or tetramethylene, or $n_1$ represents 0, $n_2$ represents 1, Z represents imino or lower alkylimino and simultaneously A represents ethylene, and their pharmaceutically acceptable acid addition salts. The invention relates above all to compounds of the formula I wherein $R_1$ represents an aliphatic hydrocarbon having a maximum of 8 carbon atoms, or a cycloaliphatic hydrocarbon radical having a maximum of 12 carbon atoms, $R_2$ represents phenyl which is unsubstituted or substituted as defined in the foregoing, or represents thienyl which is unsubstituted or substituted by lower alkyl and/or by halogen up to atomic number 35, and $R_3$ represents hydrogen, $R_4$ and $R_5$, if present, have the aforesaid meanings, and $m_1$ and $m_2$ have the meanings given under the formula I, A represents ethylene, trimethylene or tetramethylene, $n_1$ represents 1 and $n_2$ represents 0 and hence Z is omitted, and to their pharmaceutically acceptable acid addition salts. The invention primarily relates to compounds of the formula I wherein $R_1$ represents a preferably saturated aliphatic hydrocarbon radical which has a maximum of 8 carbon atoms and which is preferably bound by way of a secondary or tertiary carbon atom, or a preferably saturated cycloaliphatic hydrocarbon radical which has a maximum of 12 carbon atoms and which preferably contains a maximum of two rings, particularly a saturated cycloaliphatic hydrocarbon radical having 5 to 12 carbon atoms, $R_2$ represents phenyl which is unsubstituted or substituted by methyl, methoxy or halogen up to atomic number 35, or represents thienyl, $R_3$ represents hydrogen, $R_4$, if present, represents lower alkyl, or together with $R_1$ tetra- to hexamethylene, $R_5$, if present, represents hydrogen or lower alkyl and A represents trimethylene, tetramethylene and especially ethylene, $m_1$ and $m_2$ have the meanings given under formula I, $n_1$ represents 1 and $n_2$ represents 0 and hence Z is omitted, such as 2-[2-(cyclohexyl-imino)-2-phenyl-ethylidene]-pyrrolidine and 2-[2-(cis-2-cyclohexylcyclopentylimino)-2-phenyl-ethylidene]-pyrrolidine, and to the pharmaceutically acceptable acid addition salts of these compounds.

The compounds of the general formula I and their acid addition salts are produced according to the invention by a process in which a. a compound of the general formula II

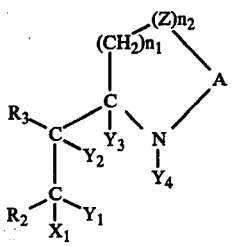
(II)

wherein $X_1$ represents lower alkoxy or together with $Y_1$ the oxo radical, $Y_1$ represents lower alkoxy, together with $Y_2$ an additional bond, or together with $X_1$ the oxo radical, and $Y_2$ represents hydrogen, or together with $Y_1$ or $Y_3$ an additional bond, $Y_3$ represents together with $Y_2$ or $Y_4$ an additional bond, and $Y_4$ represents hydrogen, lower alkyl, or together with $Y_3$ an additional bond, and $R_2$, $R_3$, A, Z, $n_1$ and $n_2$ have the meanings given under formula I, is reacted with a compound of the general formula III

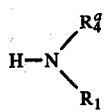
(III)

wherein $R_4{}^a$ has the meaning given for $R_4$ under the formula I, but always represents hydrogen in the case where $Y_4$ represents lower alkyl in the compound of the general formula II, and $R_1$ has the meanings given under the formula I; or b. a compound of the general formula IV

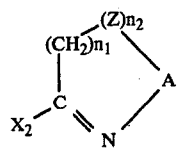
(IV)

wherein $X_2$ represents a group that can be split off, particularly lower alkoxy, lower alkylthio or halogen, especially chlorine, and A, Z, $n_1$ and $n_2$ have the meanings given under the formula I, or an acid addition salt thereof, is reacted with a compound of the general formula V

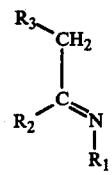
(V)

wherein $R_1$, $R_2$ and $R_3$ have the meanings given under the formula I, or with an acid addition salt thereof; and/or c. in a resulting compound of the general formula I, in which a hydrogen atom is present as $R_4$ or $R_5$, or in a compound corresponding thereto, which contains a hydrogen atom instead of the radical $R_1$, the hydrogen atom, or the two said hydrogen atoms, is, or are, replaced by lower alkyl; and, optionally, a resulting compound of the general formula I is converted into an acid addition salt, or the compound of the general formula I is liberated from an acid addition salt obtained.

In accordance with the definition for $Y_3$ in the starting materials of the general formula II, there is always at least one double bond present, either in semicyclic or in cyclic position. In the latter case, $Y_1$ and $Y_2$ can together represent an additional bond. Starting materials of the general formula II which contain only one single double bond and no lower alkyl group as $Y_4$ need not be homogeneous with regard to the position of the double bond; on the contrary, an additional bond of $Y_3$ can be formed both with $Y_2$ and with $Y_4$. The reaction of compounds of the general formula II with compounds of the general formula III is preferably performed in the presence of a condensation agent. Suitable condensation agents for the reaction according to (a) are, in particular, strong acids, especially mineral acids or organic sulphonic acids, as well as Lewis acids. There may be mentioned as examples of mineral acids: tetrafluoroboron hydride, hydrochloric acid and perchloric acid; as examples of organic sulphonic acids: methanesulphonic acid and p-toluenesulphonic acid; and as examples of Lewis acids: zinc chloride, boron trifluoride, particularly as etherate, and phosphorus oxychloride. The mineral acids and organic sulphonic acids are introduced into the reaction optionally in the form of corresponding addition salts of one of the two starting materials; for example, the salts of tetrafluorocarbon hydride obtained in a process subsequently described for producing compounds of the general formula II having lower alkoxy, especially ethoxy, as $X_1$ are used for the reaction; or the starting materials of the general formula III are used in the form of their hydrochlorides or, optionally, in the form of their perchlorates. As the reaction medium, it is possible to use for example an excess of the compound of the general formula III to be reacted, or an inert organic solvent, particularly a liquid aromatic hydrocarbon, such as benzene, toluene or xylene, or a mixture of xylenes. With the use of such hydrocarbons, the formed water or the liberated alcohol can, if required, be azeotropically distilled off, so that employment of a condensation agent becomes unnecessary or the amount thereof can be reduced. The reaction temperature is for example between 50° and 160° C., preferably between 60° and 120° C., and within this range the reaction is performed, in particular, at the boiling temperature of the reaction mixture. The reaction with low-boiling starting materials can be performed if necessary in a closed vessel.

In the starting materials of the general formula IV for the process (b), $X_2$ is, in particular, lower alkoxy, e.g. methoxy, butoxy and especially ethoxy. $X_2$ as lower alkylthio is in particular ethylthio and especially methylthio; and as halogen it is, e.g., bromine and particularly chlorine. The reactions according to (b) are performed essentially under the same reaction conditions as for (a) and likewise preferably in the presence of the condensation agents mentioned under (a), particularly methanesulphonic acid, provided that one of the two starting materials is not used in the form of an addition salt with a strong acid, especially a mineral acid or an organic sulphonic acid. The reaction temperature is preferably between 70° and 150° C.; it is particularly about 100° C. A solvent or diluent is not absolutely necessary; in some cases it is of advantage not to use one. It is possible to use if desired, instead of the aforementioned solvents, polar solvents, such as dimethylformamide, dimethylsulphoxide or N,N,N',N',N'',N''-hexamethylphosphoric acid triamide.

The introduction of one or two lower alkyl radicals instead of a hydrogen atom $R_4$ or $R_5$, and optionally of a hydrogen atom present in place of $R_1$ according to (c), can be performed in a manner known per se, for example by reaction of a reaction product of process (a) or (b), already embraced by the general formula I, or of a corresponding compound containing a hydrogen atom instead of $R_1$, with a reactive ester of a lower alkanol, particularly with a corresponding hydrohalic acid ester, lower alkanesulphonic acid ester or arenesulphonic acid ester, especially with a lower alkyl iodide or lower alkyl bromide, such as methyl iodide or ethyl iodide or propyl bromide or butyl bromide, in the presence or absence of an organic solvent, e.g. a lower alkanol such as methanol, ethanol or isopropanol, a lower alkanone such as acetone or 2-butanone, a lower alkanoic acid ester or lower alkanoic acid amide, such as ethyl acetate or dimethylformamide, or a low-boiling hydrocarbon or polyhalogenated hydrocarbon such as benzene, toluene or methylene chloride; and optionally of an acid-binding agent, e.g. a tertiary organic base or a weak inorganic base, such as triethylamine, ethyldiisopropylamine or potassium or sodium carbonate or potassium or sodium bicarbonate, preferably at temperatures between 0° C. and 120° C., and if necessary in a closed vessel, particularly however at room temperature up to the boiling temperature of the reaction mixture.

A further process known per se for the introduction of one or two lower alkyl radicals, especially methyl radicals, is the reaction of a compound of the general formula I, wherein $R_4$ or $R_5$ is a hydrogen atom, or of a corresponding compound having a hydrogen atom instead of $R_1$, with a lower oxoalkane, particularly with formaldehyde, in a reducing medium, especially in formic acid, at moderately elevated temperatures, preferably at 80–100° C.

The starting materials of the general formula II wherein $X_1$ together with $Y_1$ represents the oxo radical and $Y_3$ with $Y_2$ or $Y_4$ represents an additional bond, whilst the remaining symbols have the meanings given under the formula I or the formula II, are obtained for example by reaction of compounds of the general formula VI

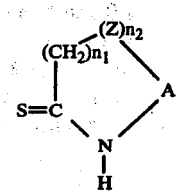

wherein A, Z, $n_1$ and $n_2$ have the meanings given under the formula I, with halogenated ketones of the general formula VII

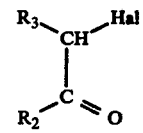

wherein
"Hal" represents a halogen atom, especially chlorine and in particular bromine,
and $R_2$ and $R_3$ have the meanings given under the formula I, to form compounds of the general formula VIII

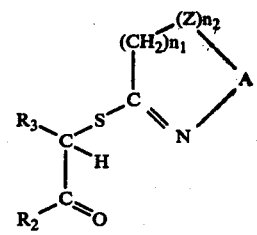

wherein $R_2$, $R_3$, A, Z, $n_1$ and $n_2$ have the meanings given under the formula I; followed by splitting-off of sulphur, for example by heating with triethylphosphite in the presence or absence of a diluting agent, such as toluene, to moderately elevated temperatures of, for example, 60°–90° C.; and optionally subsequent introduction of a lower alkyl radical $R_5$, e.g. by reaction with a reactive ester of a lower alkanol, especially with a lower alkyl halide.

By a further process are obtained compounds embraced by the general formula II wherein X together with $Y_1$ represents the oxo radical, $R_3$ has the meanings given under the formula I with the exception of lower alkyl, and the remaining symbols have the meanings given under the formula I or the formula II, which process comprises condensing lactim ethers, embraced by the general formula IV, of the general formula IX

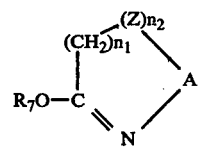

wherein
$R_7$ represents lower alkyl, particularly methyl or ethyl, and A, Z, $n_1$ and $n_2$ have the meanings given under the formula I, with compounds of the general formula X

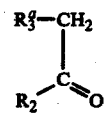

wherein
$R_3{}^a$ represents a radical corresponding to the definition of
$R_3$ given under the formula I with exception of hydrogen and lower alkyl, and
$R_2$ has the meaning given under the formula I;
and, optionally, splitting off a group $R_6$—CO, present in the resulting compound embraced by the general formula II, by treatment with a sodium lower alkoxide, preferably in the corresponding lower alkanol, in benzene or toluene; and/or introducing a lower alkyl radical $R_5$, as mentioned above.

Compounds of the general formula II wherein $X_1$ together with $Y_1$ represents the oxo radical, $Y_2$ represents hydrogen, $Y_3$ with $Y_4$ represents an additional bond, $n_1$ represents O, $n_2$ represents 1 and Z represents imino or lower alkylimino, and $R_2$, $R_3$ and A have the meanings given under the formula I, can be obtained for example, also in a manner known per se, by reaction of imido ester hydrohalides of the general formula XI

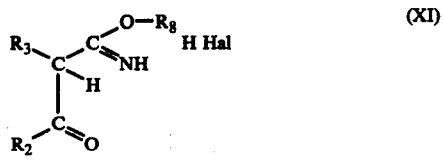

wherein
$R_8$ represents lower alkyl, particularly methyl or ethyl, and "Hal" represents chlorine or bromine, and
$R_2$ and $R_3$ have the meanings given under the formula I, with bifunctional compounds of the general formula XII

wherein
Aa represents an optionally branched-chain lower alkylene having 2 to 4 chain members, and
$R_8$ represents hydrogen or lower alkyl, particularly with 1,2-ethanediamine [see in this respect, for example, J. Klosa, Arch. Pharm. 286, 397–401 (1953)].

The ketones embraced by the general formula II, which are obtained by the aforementioned processes or by other processes known per se, are optionally converted in a manner known per se into their lower alkyl enol ethers or into their di-lower-alkyl ketals, i.e. into compounds of the general formula II with lower alkoxy as $X_1$ and an additional bond as $Y_1+Y_2$, or lower alkoxy as $Y_1$ and hydrogen as $Y_2$. For example, there are obtained by reaction of the aforementioned ketones with triethyloxonium-tetrafluoroborate in an inert organic solvent, such as methylene chloride, and in the cold state, starting materials of the general formula II wherein $X_1$ represents ethoxy and $Y_1$ and $Y_2$ together represent an additional bond. The tetrafluoroborates initially obtained from this reaction can, as already mentioned, be reacted directly with starting materials of the general formula III.

Some representatives of the starting materials of the general formula IV for the process (b) are known, and others can be produced by methods analogous to those for producing the known starting materials. Also of the starting materials of the general formula V, some are known and others are obtainable analogously, e.g. by reaction of corresponding ketones with amines corresponding to the definition for $R_1$, particularly in the presence of an acid catalyst, such as a catalytic amount of p-toluenesulphonic acid, preferably in a solvent azeotropically distilling with water, such as in toluene, at the boiling temperature thereof with continuous removal of the liberated water.

Starting materials for the process (c), which are embraced by the general formula I, can be produced for example by the process (a) or (b). Corresponding starting materials having a hydrogen atom instead of $R_1$ are obtained for example analogously to the process (a) if anhydrous ammonia is used in place of a compound of the general formula III; for example, the tetrafluoroborate of a compound of the general formula II wherein $X_1$ represents lower alkoxy, especially ethoxy, and $Y_1$ and $Y_2$ as well as $Y_3$ and $Y_4$ together represent in each case an additional bond, and $R_2$, $R_3$, A, Z, $n_1$ and $n_2$ have the meanings given under the formula I, is reacted with anhydrous ammonia in anhydrous methanol at room temperature or at a moderately elevated temperature, and the formed tetrafluoroborate of the imino compound is deprotonised, e.g., with potassium-tert.-butoxide in tert.-butanol at moderately elevated temperature, e.g. at about 60° C. [see Helv. Chim. Acta 54, 710–734, especially 722–723 (1971)].

The present invention relates also to modifications of the aforementioned processes and to the preliminary stages thereof, wherein a process is interrupted at some stage, or where a compound occurring as an intermediate at some stage is used as starting material and the uncompleted steps are performed, or wherein a starting material is formed under the reaction conditions, or, optionally, is used in the form of a salt. If the required starting materials are optically active, both the racemates and the isolated antipodes can be used, or in the case of diastereomeric compounds, it is possible to use mixtures of racemates or specific racemates, or likewise isolated antipodes. Such starting materials can also be used, if required, in the form of salts.

There are preferably used such starting materials of the general formula II and III or IV and V which yield the compounds of the general formula I which have been particularly emphasised in the foregoing.

If the final materials are obtained as racemates or as mixtures of racemates, these can within the scope of the present invention be, if required, separated and resolved into their antipodes.

The compounds of the general formula I which are obtained by the process according to the invention are optionally converted, in the customary manner, into their addition salts with inorganic and organic acids. For example, the acid desired as salt component is added to a solution of a compound of the general formula I in an organic solvent. There are preferably used for the reaction organic solvents in which the formed salt is difficultly soluble, so that it can be separated by filtration. The crystallisation of the salt is if necessary effected or completed by the addition of a second solvent. Such solvents or mixtures are, e.g., ethyl acetate, methanol, ethanol, isopropanol, ether, acetone, methyl ethyl ketone, acetone/ether, acetone/ethanol, methanol/ether or ethanol/ether.

It is possible to use as pharmaceutical active substances, instead of free bases, pharmaceutically acceptable acid addition salts, i.e. salts with acids of which the anions are not toxic in the dosage amounts concerned. Furthermore, it is of advantage if the salts to be used as pharmaceutical active substances readily crystallise and are not, or only slightly, hygroscopic. For salt formation with compounds of the formula I, it is possible to use, e.g., hydrochloric acid, hydrobromic acid, sulphuric acid, phosphoric acid, methanesulphonic acid, ethanesulphonic acid, 2-hydroxyethanesulphonic acid, acetic acid, lactic acid, succinic acid, fumaric acid, maleic acid, malic acid, tartaric acid, citric acid, benzoic acid, salicyclic acid, phenylacetic acid, mandelic acid or embonic acid.

The new imino compounds of the formula I and their pharmaceutically acceptable acid addition salts are preferably administered orally. The daily doses vary between 0.5 and 30 mg/kg for mammals; and for these of about 70 kg in weight, depending on the individual condition and age, the daily doses are between 50 and 1000 mg, especially between 150 and 500 mg. Suitable oral dosage units, e.g. dragees or tablets or capsules, preferably contain 50 to 500 mg, particularly 50 to 250 mg, of an active substance according to the invention, i.e. of a compound of the formula I or of a pharmaceutically acceptable acid addition salt thereof, together with pharmaceutical carrier substances. These dosage units are produced by combining the active substance with, e.g., solid pulverulent carriers such as lactose, saccharose, sorbitol or mannitol; starches such as potato starch, maize starch or amylopectin, also laminaria powder or citrus pulp powder; cellulose derivatives or gelatine, optionally with the addition of lubricants, such as magnesium or calcium stearate or polyethylene glycols, to form tablets or dragee cores. The dragee cores are coated, for example, with concentrated sugar solutions which can also contain, e.g., gum arabic, talcum and/or titanium dioxide, or with a lacquer dissolved in readily volatile organic solvents or solvent mixtures. Dyestuffs may be added to these coatings, e.g. for identification of the various dosage amounts. Further suitable oral dosage units are hard gelatine capsules, as well as soft closed capsules made from gelatine and a softener such as glycerin. The hard gelatine capsules contain the active substance preferably as a granulate, e.g. in admixture with lubricants such as talcum or magnesium stearate, and optionally stabilisers such as sodium metabisulphite or ascorbic acid. Also applicable are oral preparations which are not divided into dosage units, such as syrups or shakes, which likewise can be produced by combination with pharmaceutical carriers in the usual manner.

The following instructions are intended to further illustrate the production of tablets:

500.0 g of 2-[2-(cyclohexylimino)-2-phenyl-ethylidene]-pyrrolidine-(1:1)-fumarate is mixed with 500 g of lactose and 340 g of potato starch; the mixture is moistened with an alcoholic solution of 10 g of gelatine and is then granulated through a sieve. After drying of the granulate, 60 g of potato starch, 60 g of talcum, 10 g of magnesium stearate and 20 g of highly dispersed silicon dioxide are mixed in, and the mixture is subsequently pressed to form 10,000 tablets each weighing 150 mg and each containing 50 mg of active substance; the tablets can be provided with grooves to effect a more precise adjustment of the dosage amount.

In place of the aforementioned active substance, it is also possible to use, e.g., 500.0 g of 2-[2-(cis-2-cyclohexylcyclopentylimino)-2-phenyl-ethylidene]-pyrrolidine-methanesulphonate-(1:1).

The following Examples further illustrate the production of the new compounds of the general formula I and of starting materials not hitherto known; but in no way are they intended to limit the scope of the invention. The temperatures are given in degrees Centigrade.

EXAMPLE 1

9.1 g (0.03 mole) of 2-(2-ethoxy-2-phenyl-ethenyl)-1-pyrroline-tetrafluoroborate is dissolved in 30 ml of cyclohexylamine, and the clear solution is heated at 105° for 6 hours. The excess cyclohexylamine is subsequently distilled off as far as possible in a rotary evaporator; the residue is dissolved in methylene chloride; and the solution, with the addition of ice, is repeatedly extracted with 1N sodium hydroxide solution for liberation of the bases and removal of the tetrafluoroboron hydride. The organic phase is dried over sodium sulphate, concentrated by evaporation, and the residue is concentrated twice with toluene in vacuo to remove the residual cyclohexylamine. The oil remaining is taken up in isopropanol, and a warm solution of 3 g of fumaric acid in 30 ml of isopropanol is added. The formed salt is filtered off, and recrystallised from ethanol to obtain 2-[2-(cyclohexylimino)-2-phenyl-ethylidene]-pyrrolidine-(1:1)-fumarate, m.p. 202°–203°.

The 2-(2-ethoxy-2-phenyl-ethenyl)-1-pyrroline-tetrafluoroborate used as starting material is produced as follows:

a. 101.2 g (1.0 mole) of 2-pyrrolidinethione is dissolved in 300 ml of chloroform. A solution of 210 g (1.05 moles) of 2-bromoacetophenone in 400 ml of chloroform is slowly added dropwise with ice cooling. There is soon formed a thick crystal sludge, which is stirred overnight at room temperature. It is then cooled again in the ice bath; the hydrobromide of the reaction product, which has crystallised out, is filtered off and the filter residue is washed with a chloroform/hexane mixture 1:3. To liberate the 2-[(2-pyrrolin-2-yl)-thio]-acetophenone, the hydrobromide is dissolved in about 1000 ml of ice water; the solution is stirred with 100 ml of methylene chloride, and saturated sodium bicarbonate solution is added until the aqueous phase permanently shows an alkaline reaction. The organic phase is separated; the aqueous phase is extracted twice with methylene chloride, and each organic phase is washed once with saturated sodium chloride solution. The organic phases are subsequently combined, dried over sodium sulphate and concentrated at about 40° in a rotary evaporator, whereupon the crude 2-[(1-pyrrolin-2-yl)-thio]-acetophenone remains behind in the form of yellow oil. This is then dried for about 30 minutes at room temperature under high vacuum.

b. The crude product obtained according to (a) is dissolved in a mixture of 1000 ml of toluene and 190 ml of triethylphosphite, and the mixture is heated under nitrogen at 60° for 16 hours. The dark solution is concentrated as far as possible in the rotary evaporator, and the residue is stirred at room temperature with 350 ml of ether. The suspension is filtered; the residue is washed with ether and subsequently recrystallised from acetone to obtain 2-(2-pyrrolidinylidene)-acetophenone, m.p. 115°–116°.

c. 62.7 g (0.33 mole) of triethyloxonium-tetrafluoroborate is dissolved in 120 ml of methylene chloride, and the solution is cooled in an ice bath. In the course of about 30 minutes, a second solution of 56.2 g (0.3 mole) of 2-(2-pyrrolidinylidene)-acetophenone in 150 ml of methylene chloride is added dropwise. The reaction mixture is stirred at 0° for 3 hours. Approximately half of the solvent is subsequently distilled off in the rotary evaporator. On addition of 400 ml of ethyl acetate to the resulting concentrate, the crude 2-(ethoxy-2-phenyl-ethenyl)-1-pyrroline-tetrafluoroborate, m.p. 122°–123°, precipitates. After drying in vacuo at 60°, the product is further employed without additional purification.

EXAMPLE 2

62.7 g (0.33 mole) of triethyloxoniumtetrafluoroborate is dissolved in 120 ml of methylene chloride, and the solution is cooled in an ice bath. A solution of 66.5 g (0.3 mole) of p-chloro-2-(2-pyrrolidinylidene)-acetophenone in 300 ml of methylene chloride is added dropwise within 30 minutes. The reaction mixture is stirred at 0° for 3 hours; the methylene chloride is subsequently evaporated off at 30° in a rotary evaporator, and the oily residue is dried at room temperature under high vacuum. The resulting crude 2-[2-(p-chlorophenyl)-2-ethoxy-ethenyl]-1-pyrrolidine-tetrafluoroborate is directly dissolved in 200 ml of cyclohexylamine. The brown solution is heated for 2½ hours at 100°, and the excess cyclohexylamine is subsequently evaporated off in the rotary evaporator. The salt mixture remaining behind is taken up in methylene chloride and the solution, with the addition of ice, is repeatedly extracted with 1N sodium hydroxide solution. The organic phase is dried over sodium sulphate, concentrated by evaporation, and the residue is repeatedly concentrated with a small amount of toluene in vacuo in order to remove the residual cyclohexylamine. The oil remaining behind is dried under high vacuum and subsequently dissolved in ethanol, and a hot solution of about 25 g of fumaric acid in ethanol is added. The resulting salt is filtered off and recrystallised from isopropanol to yield 2-[2-(4-chlorophenyl)-2-(cyclohexylimino)-ethylidene]-pyrrolidine-fumarate, m.p. 209°–210° (decomposition).

With the use of 76.8 g (0.3 mole) of 3',4'-dichloro-2-(2-pyrrolidinylidene)-acetophenone, there is obtained in an analogous manner 2-[2-(3,4-dichlorophenyl)-2-(cyclohexylimino)-ethylidene]-pyrrolidine-(1:1)-fumarate, m.p. 208°–209° (from isopropanol/ether).

The p-chloro-2-(2-pyrrolidinylidene)-acetophenone used as starting material is produced as follows:

a. A solution of 73.5 g (0.315 mole) of 2-bromo-p-chloroacetophenone in 350 ml of chloroform is slowly added dropwise, with ice cooling, to a solution of 30.4 g (0.3 mole) of 2-pyrrolidinethione in 100 ml of chloroform. There is formed a thick crystal slurry, which is stirred for a further 4 hours at room temperature. The reaction mixture is cooled afresh in the ice bath; the hydrobromide of the reaction product is filtered off and the residue is washed with a chloroform/hexane mixture 1:3. In order to liberate the p-chloro-2-[(1-pyrrolin-2-yl)-thio]-acetophenone, the crystalline residue is suspended in about 500 ml of ice water; it is stirred with 300 ml of methylene chloride, and saturated sodium bicarbonate solution is added until the aqueous phase permanently shows an alkaline reaction. The aqueous phase is separated and extracted twice with methylene chloride. The organic phases are combined, washed once with saturated sodium chloride solution, dried over sodium sulphate and concentrated at about 40° in the rotary evaporator, whereupon the crude, gradually crystallising p-chloro-2-[(1-pyrrolin-2-yl)-thio]-acetophenone remains behind. It is subsequently dried at room temperature under high vacuum.

b. The reaction product obtained according to (a) is dissolved in 120 ml of triethylphosphite, and the solution is heated at 60° for 40 minutes, with the reaction product commencing to precipitate already after 10 minutes. After completion of the reaction, the reaction mixture is cooled in an ice bath; it is then filtered and the residue is washed with ether. Recrystallisation of the residue from isopropanol yields p-chloro-2-(2-pyrrolidinylidene)-acetophenone, m.p. 146°–147° C.

3',4'-Dichloro-2-(2-pyrrolidinylidene)-acetophenone, m.p. 148°–149°, is obtained analogously to (a) and (b).

EXAMPLE 3

By refluxing the solution of 9.1 g (0.03 mole) of 2-(2-ethoxy-2-phenyl-ethenyl)-1-pyrroline-tetrafluoroborate in 30 ml of isopropylamine for 1 hour and processing analogously to Example 1, there is obtained crude 2-[2-(isopropylimino)-2-phenylethylidene]-pyrrolidine. The crude base is dissolved in isopropanol, and 2.8 g of methanesulphonic acid is added, whereupon 2-[2-(isopropylimino)-2-phenyl-ethylidene]-pyrrolidine-(1:1)-methanesulphonate, m.p. 175°–176° (decomposition) crystallises out.

EXAMPLE 4

By heating the solution of 9.1 g (0.03 mole) of 2-(2-ethoxy-2-phenyl-ethenyl)-1-pyrroline-tetrafluoroborate in 50 ml of tert.-butylamine in a closed tube at 105° for 18 hours and processing analogously to Example 1, there is obtained crude 2-[2-phenyl-2-(tert.-butylimino)-ethylidene]-pyrrolidine. The crude base is dissolved in ether, and 2.8 g of methanesulphonic acid is added, whereupon 2-[2-phenyl-2-(tert.-butylimino)-ethylidene]-pyrrolidine-(1:1)-methanesulphonate crystallises out. It melts at 208°–209° (decomposition) after recrystallisation from ethyl acetate.

EXAMPLE 5

By heating the solution of 9.1 g (0.03 mole) of 2-(2-ethoxy-2-phenyl-ethenyl)-1-pyrroline-tetrafluoroborate in 25 ml of aniline for 1 hour at 80° and processing analogously to Example 1, there is obtained crude 2-[2-phenyl-2-(phenylimino)-ethylidene]-pyrrolidine. An addition of 2.8 g of methanesulphonic acid is made to a solution of the crude base in ethyl acetate and the resulting crystals are filtered off. The product thus obtained is 2-[phenyl-2-(phenylimino)-ethylidene]-pyrrolidine-(1:1)-methanesulphonate, m.p. 193°–194° (decomposition).

EXAMPLE 6

The solution of 9.1 g (0.03 mole) of 2-[2-ethoxy-2-phenyl-ethenyl]-1-pyrroline-tetrafluoroborate in 25 ml of diethylamine is refluxed for 12 hours; it is then processed analogously to Example 1 to yield crude 2-[2-(diethylamino)-2-phenyl-ethenyl]-1-pyrroline. By the addition of 2.8 g of methanesulphonic acid to the solution of the crude base in isopropanol, removal of the crystals by filtration and recrystallisation from isopropanol, there is obtained 2-[2-(diethylamino)-2-phenylethenyl]-1-pyrroline-(1:1)-methanesulphonate, m.p. 143°–145° (decomposition).

EXAMPLE 7

9.1 g (0.03 mole) of 2-[2-ethoxy-2-phenyl-ethenyl]-1-pyrroline-tetrafluoroborate is dissolved in 11.2 g (0.06 mole) of 1,1-diphenylmethylamine, and the solution is heated at 110° for 30 minutes, whereupon the tetrafluoroborate of the reaction product precipitates directly. The reaction mixture is cooled, diluted with ethyl acetate and filtered. The crystallised filter residue is suspended in methylene chloride; and for liberation of the base and removal of the tetrafluoroboron hydride it is repeatedly extracted with 1N sodium hydroxide solution. The crude 2-[2-[(diphenylmethyl)-imino]-2-phenylethylidene]-pyrrolidine remaining after the methylene chloride has been evaporated off is dissolved in ethyl acetate, and 2.8 g of methanesulphonic acid is added. The salt precipitating in crystalline form is purified by recrystallisation from isopropanol to yield 2-[2-[(diphenylmethyl)-imino]-2-phenylethylidene]-pyrrolidine-(1:1)-methanesulphonate, m.p. 212°–213° (decomposition).

EXAMPLE 8

9.9 g (0.03 mole) of 2-(2-ethoxy-2-phenyl-ethenyl)-4,5,6,7-tetrahydro-3H-azepine-tetrafluoroborate is dissolved in 50 ml of isopropylamine, and the solution is refluxed for 18 hours. The excess isopropylamine is then distilled off, the residue is dissolved in methylene chloride, and the solution, with the addition of ice, is extracted twice with 1N sodium hydroxide solution and washed once with water. The organic phase is dried over sodium sulphate and concentrated by evaporation. The crude 2-[2-(isopropylimino)-2-phenylethylidene]-hexahydro-1H-azepine remaining behind as oil is dissolved in ethyl acetate. The salt, precipitated after the addition of 2.8 g of methanesulphonic acid, is purified by recrystallisation from acetone to obtain 2-[2-(isopropylimino)-2-phenyl-ethylidene]-hexahydro-1H-azepine-(1:1)-methanesulphonate, m.p. 155°–157° (decomposition).

The 2-[2-ethoxy-2-phenyl-ethenyl]-4,5,6,7-tetrahydro-3H-azepine-tetrafluoroborate used as starting material is produced as follows:

a. A solution of 21 g (0.105 mole) of 2-bromoacetophenone in 50 ml of methylene chloride is slowly added dropwise at room temperature to a solution of 10.1 g (0.1 mole) of hexahydro-2H-azepine-2-thione in 100 ml of methylene chloride. The solution is stirred for 18 hours at room temperature; ice is subsequently added and the solution is washed twice with saturated sodium bicarbonate solution and once with saturated sodium chloride solution; it is subsequently dried over sodium sulphate and filtered. The filtrate is allowed to stand for 4 hours at room temperature, during which time the colour changes from yellow to red, and the splitting-off of sulphur from the initially formed 2-[(hexahydro-2H-azepin-2-yl)-thio]-acetophenone becomes completed. The solvent is then evaporated off in vacuo; the residue is taken up in ether; the solution is stirred twice in succession with active charcoal, filtered and the filtrate is concentrated by evaporation to approximately 100 ml. On cooling of this solution in an ice/sodium chloride bath, 2-(hexahydro-2H-azepin-2-ylidene)-acetophenone crystallises out. After recrystallisation from ether/hexane, it melts at 73°–74°.

b. 60 g (0.315 mole) of triethyloxonium-tetrafluoroborate and 64.8 g (0.30 mole) of 2-(hexahydro-2H-azepin-2-ylidene)-acetophenone are dissolved in 500 ml of methylene chloride. The reaction mixture is allowed to stand for 48 hours at room temperature; it is subsequently concentrated by evaporation to a small volume and ethyl acetate is added to the oil remaining, whereupon crude 2-(2-ethoxy-2-phenyl-ethenyl)-4,5,6,7-tetrahydro-3H-azepine-tetrafluoroborate, m.p. 136°–138° (decomposition), crystallises out. After drying at 50° in vacuo, this product can be further used directly.

EXAMPLE 9

8.8 g (0.03 mole) of 2-[2-ethoxy-2-(2-thienyl)-ethenyl]-1-pyrroline-tetrafluoroborate is dissolved in 30 ml of isopropylamine. The solution is refluxed for 18 hours, and the excess isopropylamine is thereupon evaporated off in a rotary evaporator. The brown residue is dissolved in methylene chloride, ice is added, the solution is extracted twice with 1N sodium hydroxide solution, dried over sodium sulphate and concentrated by evaporation. The crude 2-[2-(isopropylimino)-2-(2-thienyl)-ethylidene]-pyrrolidine, which is obtained as gradually crystallising oil, is dissolved in ethyl acetate, and to the solution is added 2.8 g of methanesulphonic acid. The precipitated salt is filtered off and recrystallised from isopropanol/ether to obtain 2-[2-(isopropylimino)-2-(2-thienyl)-ethylidene]-pyrrolidine-(1:1)-methanesulphonate, m.p. 144°–146° (decomposition). The 2-[2-ethoxy-2-(2-thienyl-ethenyl]-1-pyrroline used as starting material is produced as follows:

a. To a solution of 30.3 g (0.3 mole) of 2-pyrrolidinethione in 200 ml of methylene chloride, there is slowly added dropwise in the course of 30 minutes, with ice cooling, a solution of 74 g (0.76 mole) of freshly prepared 2-(bromoacetyl)-thiophene [J.Amer.Chem.Soc. 71, 10 (1949); see also Houben-Weyl 4th edition, vol. 5/4, page 182] in 100 ml of carbon tetrachloride, whereupon a light-brown precipitate immediately forms. The reaction mixture is stirred at room temperature for a further 20 minutes, and the precipitate is subsequently filtered off and washed with methylene chloride. In order to liberate the base, the crude hydrobromide is suspended in methylene chloride, ice is added, and the suspension is stirred with saturated sodium bicarbonate solution being slowly added until the water phase shows a permanent alkaline reaction. The organic phase is subsequently separated, dried over sodium sulphate and concentrated at about 40° in the rotary evaporator, whereupon 2-[[2-(1-pyrrolin-2-yl)-thio]-acetyl]-thiophene remains behind in the form of brown oil.

b. The crude product obtained according to a) is dissolved in a mixture of 250 ml of toluene and 50 ml of triethylphosphite and the solution is heated at 80° for 2½ hours. By the cooling of the reaction mixture in an ice bath, the reaction product is caused to crystallise out; it is subsequently filtered off and washed with ether. Recrystallisation from ethyl acetate/hexane yields 2-[2-(2-pyrrolidinylidene)-acetyl]-thiophene, m.p. 149°–150°.

c. 5.5 g (0.03 mole) of 2-[2-(2-pyrrolidinylidene)-acetyl]-thiophene and 6.26 g (0.033 mole) of triethyloxonium-tetraborofluorate are dissolved together in 30 ml of methylene chloride, and the solution is stirred at room temperature for 2½ hours. The reaction product is then precipitated by the addition of about 100 ml of ethyl acetate; it is filtered off and washed with ethyl acetate. Recrystallisation from acetone/hexane yields 2-[2-ethoxy-2-(2-thienyl)-ethenyl]-1-pyrroline-tetrafluoroborate, m.p. 148°–151° (decomposition), which, after drying at 50° in vacuo, is further used directly.

EXAMPLE 10

Crude 2-[2-(1-piperidyl)-2-phenyl-ethenyl]-1-pyrroline is produced by refluxing for 12 hours the solution of 9.1 g (0.03 mole) of 2-(2-ethoxy-2-phenyl-ethenyl)-1-pyrroline-tetrafluoroborate in 25 ml of piperidine, and processing the reaction mixture analogously to Example 1. By the addition of 2.8 g of methanesulphonic acid to the solution of the crude base in isopropanol, concentration of this solution in the rotary evaporator and recrystallisation of the residue from acetone/hexane, there is obtained 2-[2-(1-piperidyl-2-phenylethenyl]-1-pyrroline-(1:1)-methanesulphonate, m.p. 123°–124°.

EXAMPLE 11

Crude 2-[2-(N-methylcyclohexylamino)-phenylethenyl]-1-pyrroline is produced by heating the solution of 9.1 g (0.03 mole) of 2-(2-ethoxy-2-phenyl-ethenyl)-1-pyrroline-tetrafluoroborate in 20 ml of N-methyl-cyclohexylamine for 2 hours at 100°, and processing the reaction mixture analogously to Example 1. By addition of 2.8 g of methanesulphonic acid to the solution of the crude base in isopropanol, evaporation of this solution in the rotary evaporator and recrystallisation of the residue from ethyl acetate, there is obtained 2-[2-(N-methyl-cyclohexylamino)-phenylethenyl]-1-pyrroline-(1:1)-methanesulphonate, m.p. 163°–164°.

EXAMPLE 12

62.7 g (0.33 mole) of triethyloxonium-tetrafluoroborate is dissolved in 120 ml of methylene chloride, and the solution is cooled in an ice bath. A solution of 65.1 g (0.3 mole) of p-methoxy-2-(2-pyrrolidinylidene)-acetophenone, m.p. 134°–135°, produced completely analogously to Example 2(a) and 2(b), in 450 ml of methylene chloride is added dropwise within 30 minutes. The reaction mixture is stirred at 0° for 3 hours; the methylene chloride is subsequently evaporated off at 30° in the rotary evaporator, and the oily brown residue is dried at room temperature under high vacuum.

The crude 2-[2-(p-methoxyphenyl-2-ethoxy-ethenyl]-1-pyrroline-tetrafluoroborate obtained in this manner is directly dissolved in 180 ml of cyclohexylamine, and the brown solution is heated at 100° for 2½ hours. Processing is carried out analogously to Example 2, whereby to the crude oily 2-[2-(p-methoxyphenyl)-2-(cyclohexylimino)-ethylidene]-pyrrolidine dissolved in 300 ml of isopropanol there is added a solution of 18.6 g of fumaric acid in isopropanol, and crystallisation is effected by the addition of acetone. After recrystallisation from an acetone/water mixture (6:1), the resulting 2-[2-(p-methoxyphenyl)-2-(cyclohexylimino)-ethylidene]-pyrrolidine-(1:1)-fumarate melts at 192°–193° (decomposition).

In an analogous manner are obtained, starting with 65.1 g (0.3 mole) of m-methoxy-2-(2-pyrrolidinylidene)-acetophenone, m.p. 93°–94°, the crude 2-( 2-(cyclohexylimino)-2-(m-methoxyphenyl)-ethylidene]-pyrrolidine and from that its (1:1)-methane-sulphonate, m.p. 137°–138° (from isopropanol/acetone).

Likewise in an analogous manner is obtained, starting with 65.1 g (0.3 mole) of o-methoxy-2-(2-pyrrolidinylidene)-acetophenone, m.p. 100°, 2-[2-(o-methoxyphenyl)-2-(cyclohexylimino)-ethylidene]-pyrrolidine, which melts at 91°–92° after recrystallisation from ligroin.

EXAMPLE 13

9.5 g (0.03 mole) of 2-[2-(p-methylphenyl)-2-ethoxy-ethenyl]-1-pyrroline-tetrafluoroborate is dissolved in 20 ml of cyclohexylamine, and the solution is heated at 100° for 2½ hours. Processing is carried out analogously to Example 2, whereby the crude crystallising 2-[2-(p-methylphenyl)-2-(cyclohexylimino)-ethylidene]-pyrrolidine is dissolved in ethanol, and to the solution is added a hot ethanolic solution of 3 g of fumaric acid. The formed salt is filtered off, and recrystallised from isopropanol to obtain 2-[2-(p-methylphenyl)-2-(cyclohexylimino)-ethylidene]-pyrrolidine-(1:1)-fumarate, m.p. 201°–202° (decomposition).

The starting material is produced as follows:

a. 62.7 g (0.33 mole) of triethyloxonium-tetrafluoroborate is dissolved in 120 ml of methylene chloride and the solution is cooled to 0°. Within 30 minutes is added dropwise a solution of 60.3 g (0.3 mole) of p-methyl-2-(2-pyrrolidinylidene)-acetophenone, m.p. 143°–144°, produced analogously to Examples 2(a) and 2(b), in 370 ml of methylene chloride. The reaction mixture is stirred at 0° for 3 hours; the methylene chloride is subsequently evaporated off at about 30° in a rotary evaporator and the yellow oily residue is crystallised from ethyl acetate. The product is filtered off, washed with ethyl acetate, dried at 50° in vacuo, and further employed without additional purification.

EXAMPLE 14

9.1 g (0.03 mole) of 2-(2-ethoxy-2-phenyl-ethenyl)-2-imidazoline-tetrafluoroborate is dissolved in 30 ml of cyclopentylamine, and the solution is heated under nitrogen at 100° for 18 hours. The excess cyclopentylamine is subsequently distilled off as far as possible in the rotary evaporator; the residue is dissolved in methylene chloride, and the solution, with the addition of ice, is repeatedly extracted with 1N sodium hydroxide solution for liberation of the bases and removal of the tetrafluoroboron hydride. The organic phase is dried over sodium sulphate, concentrated by evaporation, and the residue is concentrated twice with toluene in vacuo to effect the removal of the residual cyclopentylamine. The oil remaining behind is taken up in isopropanol, and 3 g of methane-sulphonic acid is added. The salt is precipitated by the addition of ethyl acetate, an subsequently recrystallised from pure isopropanol to obtain 2-[2-phenyl-2-(cyclopentylamino)-ethenyl]-2-imidazoline-(1:1)-methanesulphonate, m.p. 184°–186°.

The 2-(2-ethoxy-2-phenyl-ethenyl)-2-imidazoline-tetrafluoroborate is produced as follows:

20 g (0.105 mole) of triethyloxonium-tetrafluoroborate is dissolved in 200 ml of methylene chloride. To the solution is added 18.8 g (0.1 mole) of crystalline 2-(2-imidazolidinylidene)-acetophenone [m.p. 211°–212°, see J. Klosa, Arch.Pharmaz. 286, 397 (1953)]. After the slightly exothermic reaction has subsided, the reaction mixture, a clear yellow solution, is stirred for 16 hours at room temperature; it is subsequently concentrated to dryness in the rotary evaporator; and the crystallising residue is suspended in 300 ml of ethyl acetate. The suspension is cooled to 5°, and the crystals are filtered off with suction to obtain 2-(2-ethoxy-2-phenyl-ethenyl)-2-imidazoline-tetrafluoroborate, m.p. 151°–152°. After drying at 60° in vacuo, the product is further employed without additional purification.

EXAMPLE 15

20 g (0.105 mole) of triethyloxonium-tetrafluoroborate is dissolved in 100 ml of methylene chloride, and the solution is cooled in an ice bath. A solution of 22.9 g (0.1 mole) of 1-phenyl-2-(2-pyrrolidinylidene)-1,3-butanedione in 70 ml of methylene chloride is added dropwise in the course of 30 minutes. The reaction mixture is subsequently stirred for 4 hours at room temperature; the methylene chloride is evaporated off at 30° in the rotary evaporator; and the oily residue is dried under high vacuum at room temperature. The resulting crude 3-ethoxy-1-phenyl-2-(1-pyrrolin-2-yl)-2-buten-1-one-tetrafluoroborate is dissolved directly in 80 ml of cyclohexylamine, whereupon the reaction mixture heats up. It is allowed to stand for about 15 hours at room temperature, and the excess cyclohexylamine is then evaporated off in the rotary evaporator. The salt mixture remaining behind is taken up in methylene chloride, and the solution, with the addition of ice, is repeatedly extracted with 1N sodium hydroxide solution. The organic phase is dried over sodium sulphate, concentrated by evaporation, and the residue is repeatedly concentrated with a small amount of toluene in vacuo in order to remove the residual cyclohexylamine. The oil remaining is dried under high vacuum, and subsequently chromatographed on a silica-gel column with ethyl acetate as the eluant. The main fractions are combined, dissolved in isopropanol, and a hot solution of about 6 g of fumaric acid in ethanol is added. The resulting salt is filtered off and recrystallised from isopropanol. There is obtained 3-(cyclohexylamino)-1-phenyl-2-(1-pyrrolin-2-yl)-2-buten-1-one-(1:1)-fumarate, m.p. 170°-172°.

The starting material is produced as follows:

a. 9.9 g (0.1 mole) of 2-methoxy-1-pyrroline and 24.4 g (0.15 mole) of 1-phenyl-1,3-butanedione are mixed together and, in a nitrogen atmosphere, heated with stirring for 18 hours in an oil bath at 100°. The dark reaction mixture is cooled to 60° and 500 ml of hexane is added. Upon further cooling to room temperature, the reaction product crystallises out. Recrystallisation from ethyl acetate/hexane yields 1-phenyl-2-(2-pyrrolidinylidene)-1,3-butanedione, m.p. 106°-108°.

EXAMPLE 16

9.1 g (0.03 mole) of 2-(2-ethoxy-2-phenyl-ethenyl)-1-pyrroline-tetrafluoroborate is heated in 12.5 g (0.1 mole) of 3-azabicyclo[3.2.2]nonane at 110° for 30 minutes, during which the tetrafluoroborate of the reaction product precipitates out directly.

The reaction mixture is cooled, diluted with isopropanol and filtered. The crystallised filter residue is suspended in methylene chloride and, for liberation of the base and removal of the tetrafluoroboron hydride, repeatedly extracted with 1N sodium hydroxide solution. The crude 2-[2-(3-azabicyclo[3.2.2]non-3-yl)-2-phenylethenyl]-1-pyrroline, remaining behind after the methylene chloride has been evaporated off, is dissolved in acetone and to the solution is added 2.8 g of methanesulphonic acid. The salt precipitating on addition of hexane is purified by recrystallisation from acetone/hexane to yield 2-[2-(3-azabicyclo[3.2.2]non-3-yl)-2-phenyl-ethenyl]-1-pyrroline-(1:1)-methanesulphonate, m.p. 172°-173° (decomposition).

EXAMPLE 17

A mixture of 11.3 g (0.04 mole) of 2-[2-(cyclohexylimino)-2-phenyl)-ethylidene]-pyrrolidine (liberated from the fumarate obtained according to Example 1) and 30 ml of methyl iodide is stirred for 15 hours at room temperature. The formed yellow crystals are filtered off and subsequently washed with ether. The filter residue is thereupon suspended in 200 ml of methylene chloride and, for liberation of the base and removal of the hydrogen iodide, extracted three times with 100 ml of 1N sodium hydroxide solution each time. The organic phase is then concentrated by evaporation, whereupon the crude base remains behind in the form of yellow oil. This oil is dissolved in methanol; to the solution is added a methanolic solution of 2.2 g of fumaric acid, and the mixture is concentrated in vacuo in the rotary evaporator. The residue is recrystallised from isopropanol to obtain 1-methyl-2-[2-(cyclohexylimino)-2-phenyl-ethylidene]-pyrrolidine-fumarate-(1:1), m.p. 182°-183°.

EXAMPLE 18

9.1 g (0.03 mole) of 2-(2-ethoxy-2-phenyl-ethenyl)-1-pyrroline-tetrafluoroborate and 5.0 g (0.03 mole) of cis-2-cyclohexylcyclopentylamine [for production see J. Martin Grisar et al., J. Med. Chem. 16, 683, (1973)] are heated together at 100° for 2 hours. The melt is subsequently cooled, taken up in methylene chloride, and this solution is then extracted once in each case with 1N sodium hydroxide solution, with 2N potassium carbonate solution and with water. The organic phase is dried over sodium sulphate and concentrated by evaporation, and the crystallising reddish residue is briefly dried under high vacuum. The crude base is recrystallised once from isopropanol, subsequently dissolved warm in ethyl acetate, and 1.5 g of methanesulphonic acid is added. After cooling, the precipitated salt is filtered off and recrystallised from methylene chloride/ethyl acetate. The resulting 2-[2-(cis-2-cyclohexylcyclopentylimino)-2-phenyl-ethylidene]-pyrrolidine-methanesulphonate-(1:1) melts at 179°-180°.

There are obtained in an analogous manner, starting with 9.1 g (0.03 mole) of 2-(2-ethoxy-2-phenyl-ethenyl)-1-pyrrolidine-tetrafluoroborate and 4.25 g of 2-cyclohexyl-1-methylethylamine, 2-[2-[2-cyclohexyl-1-methylethyl)-imino]-2-phenyl-ethylidene]-pyrrolidine and from that its (1:1)-methanesulphonate having a melting point of 191°-192°.

EXAMPLE 19

By a process analogous to that described in Example 18, there is obtained, from 14.5 g (0.0478 mole) of 2-(2-ethoxy-2-phenyl-ethenyl)-1-pyrroline-tetrafluoroborate and 7.3 g (0.044 mole) of trans-2-cyclohexylcyclopentylamine, crude [2-[2-(trans-2-cyclohexylcyclopentylimino)-2-phenyl-ethylidene]-pyrrolidine]. The crude base is chromatographed on a short silica-gel column with methanol as the eluant. The main fractions are combined, dissolved in methanol, and to this solution is added a solution of the equimolar amount of fumaric acid in methanol. The methanolic solution is concentrated by evaporation, and the residue remaining behind is triturated with ether to obtain 2-[2-(trans-2-cyclohexylcyclopentylimino)-2-phenyl-ethylidene]-pyrrolidine-fumarate-(1:1), m.p. 157°-158° (with decomposition).

EXAMPLE 20

By the process described in Example 18, there is produced, from 4.0 g (0.013 mole) of 2-(2-ethoxy-2-phenyl-ethenyl)-1-pyrroline-tetrafluoroborate and 2.25 g (0.013 mole) of 1-cyclohexyl-2-amino-pentane, 2-[2-[1-(cyclohexylmethyl)-butyl-imino]-2-phenyl-ethylidene]-pyrrolidine-fumarate-(1:1). In the melting point tube, the slightly yellowish, hygroscopic crystals commence foaming at about 85°.

The 1-cyclohexyl-2-amino-pentane, used as starting material, can be obtained by hydrogenation of 3.7 g of 1-phenyl-2-aminopentane hydrochloride, dissolved in 100 ml of water. The catalyst used is 1.4 g of 5% rhodium-charcoal. Hydrogenation ceases after about 4½ hours at 70° and 4 bars hydrogen pressure. The resulting 1-cyclohexyl-2-amino-pentane hydrochloride melts at 130°–131°.

EXAMPLE 21

By the process described in Example 18, there is produced, from 10.4 g (0.034 mole) of 2-(2-ethoxy-2-phenyl-ethenyl)-1-pyrroline-tetrafluoroborate and 6.2 g (0.034 mole) of trans-4-cyclohexylcyclohexylamine [for production see D. V. Nightingale et al., J. Org. Chem. 17, 1017 (1952)], 2-[2-(trans-4-cyclohexylcyclohexyl-imino)-2-phenyl-ethylidene]-pyrrolidine. The crude base is chromatographed on a short silica-gel column with a chloroform/methanol mixture (volume ratio 9:1) as the eluant. The main fractions are combined and dissolved in ethanolic hydrochloric acid; the solution is concentrated by evaporation, and the residue remaining is triturated with ethyl acetate. There is obtained 2-[2-(trans-4-cyclohexylcyclohexylimino)-2-phenyl-ethylidene]-pyrrolidine hydrochloride-(1:1), m.p. 243°–244°.

EXAMPLE 22

Analogously to Example 1, there is obtained, starting with 9.5 g of 2-(2-ethoxy-2-phenyl-ethenyl)-3,4,5,6-tetrahydropyridine-tetrafluoroborate and 30 ml of cyclohexylamine, 2-[(2-phenyl-2-(cyclohexylamino)-ethenyl]-3,4,5,6-tetrahydropyridine, and from this its (1:1)-methanesulphonate, m.p. 172°–173°; and starting with 9.5 g of 2-(2-ethoxy-2-phenyl-ethenyl)-3,4,5,6-tetrahydropyridine-tetrafluoroborate and 30 ml of diethylamine, is obtained 2-[2-phenyl-2-(diethylamino)-ethenyl]-3,4,5,6-tetrahydropyridine, and from this its (1:1)-fumarate, m.p. 169°–170° (from isopropanol).

The 2-(2-ethoxy-2-phenyl-ethenyl)-3,4,5,6-tetrahydropyridine-tetrafluoroborate required as starting material is produced as follows:

a. 12.7 g (0.1 mole) of 2-ethoxy-3,4,5,6-tetrahydropyridine and 24.4 g (0.15 mole) of 1-phenyl-1,3-butanedione are mixed and heated together in a nitrogen atmosphere, with stirring, for 32 hours in an oil bath at 100°. The reaction mixture is cooled, and subsequently chromatographed on silica gel with an ethyl acetate/hexane mixture as the eluant. The main fractions are combined and crystallised from ether to obtain 1-phenyl-2-(2-piperidinylidene)-1,3-butanedione in the form of yellow crystals, m.p. 80°–81°.

b. 12.15 g (0.05 mole) of 1-phenyl-2-(2-piperidinylidene)-1,3-butanedione are introduced into a prepared solution of 3.5 g of sodium in 120 ml of ethanol. The reaction mixture is then refluxed for 40 minutes. After cooling, it is neutralised with glacial acetic acid, and filtered off from the sodium acetate. The filtrate is concentrated in the rotary evaporator, and the residue is dissolved in methylene chloride. The solution is repeatedly extracted with water; the organic phase is dried over sodium sulphate, and the solvent is evaporated off in the rotary evaporator. The oily residue is crystallised from ether/hexane to yield 2-(2-piperidinylidene)-acetophenone, m.p. 59°–60°.

c. 4.1 g (0.022 mole) of triethyloxonium-tetrafluoroborate is dissolved in 50 ml of methylene chloride, and the solution is cooled in an ice bath. Within about 15 minutes, there is added dropwise a solution of 4.2 g (0.02 mole) of 2-(2-piperidinylidene)-acetophenone in 20 ml of methylene chloride. The reaction mixture is subsequently stirred for 15 hours at room temperature. The yellow reaction solution is concentrated in the rotary evaporator to a small volume, and caused to crystallise by the addition of ethyl acetate. The precipitated crude 2-(2-ethoxy-2-phenyl-ethenyl)-3,4,5,6-tetrahydropyridine-tetrafluoroborate, m.p. 143°–144°, is dried at 60° in vacuo and subsequently further used without additional purification.

EXAMPLE 23

Analogously to Example 1 there is obtained, from 7.2 g (0.03 mole) of 2-(2-ethoxy-1-propenyl)-1-pyrrolidine-tetrafluoroborate [see Helv. Chim. Acta 54, 722 - 3 (1971)] and 30 ml of tert.-butylamine, 2-[2-(tert.-butylimino)-propylidene]-pyrrolidine, and from this its (1:1)-methanesulphonate, m.p. 154°–155° (from ethyl acetate/acetonitrile); and starting with 7.2 g (0.03 mole) of 2-(2-ethoxy-1-propenyl-1-pyrroline-tetrafluoroborate and 20 ml of N-methyl-cyclohexylamine, is obtained 2-[2-(N-methyl-cyclohexylamino)-1-propenyl]-1-pyrroline, and from this its (1:1)-fumarate, m.p. 152°–153° (from isopropanol).

EXAMPLE 24

Analogously to Example 8 there is obtained, starting with 9.9 g (0.03 mole) of 2-(2-ethoxy-2-phenyl-ethenyl)-4,5,6,7-tetrahydro-3H-azepine-tetrafluoroborate and 20 ml of cyclohexylamine, 2-[2-(cyclohexylimino)-2-phenyl-ethylidene]-hexahydro-1H-azepine, and from this its (1:1)-fumarate, m.p. 169°–170° (from isopropanol); and starting with 9.9 g (0.03 mole) of 2-(2-ethoxy-2-phenyl-ethenyl)-4,5,6,7-tetrahydro-3H-azepine-tetrafluoroborate and 40 ml of diethylamine, 2-[2-(diethylamino)-2-phenyl-ethenyl]-4,5,6,7-tetrahydro-3H-azepine, and from this its (1:1)-methanesulphonate, m.p. 122°–124° (from isopropanol).

EXAMPLE 25

Analogously to Example 14 there is obtained, starting with 9.1 g (0.03 mole) of 2-(2-ethoxy-2-phenyl-ethenyl)-2-imidazoline-tetrafluoroborate and 45 g of 2,6-dichloroaniline, crude 2-[2-phenyl-2-(2,6-dichloroanilino)-ethenyl]-2-imidazoline, and from this its (1:1)-fumarate, m.p. 207°–208° (from ethanol/ether).

EXAMPLE 26

Analogously to Example 15 there is obtained, starting with 34.5 g (0.1 mole) of crude 3-ethoxy-1-phenyl-2-(1-pyrrolin-2-yl)-buten-1-one-tetrafluoroborate and 80 ml of diethylamine, 3-(diethylamino)-1-phenyl-2-(1-pyrrolin-2-yl)-2-buten-1-one, and from this its (1:1)-fumarate.

EXAMPLE 27

By the process described in Example 18, there is produced, from 5.4 g (0.0167 mole) of 2-(1-methyl-2- ethoxy-2-phenyl-ethenyl)-1-pyrroline-tetrafluoroborate and 5 ml of cyclohexyl-amine, 2-[1-methyl-2-(cyclohexylimino)-2-phenyl-ethylidene]-pyrrolidine. The crude base is chromatographed on a short column of silica gel. Elution is performed firstly with chloroform and then with a chloroform/methanol mixture (volume ratio 9:1). The main fractions are combined and dissolved in ethanolic hydrochloric acid; the solution is concentrated by evaporation and the residue remaining is triturated with ethyl acetate. The crude hydrochloride obtained is recrystallised from an ethyl acetate/isopropanol mixture to obtain 2-[1-methyl-2-(cyclohexylimino)-2-phenyl-ethylidene]-pyrrolidine hydrochloride, m.p. 264°-265° (slight decomposition).

The starting material is produced as follows:

a. 17.0 g of α-(2-pyrrolidinylidene-acetophenone and 11.3 g of potassium-tert.-butoxide are dissolved in a mixture of 8 ml of dimethylformamide and 170 ml of benzene. A solution of 25 g of methyl iodide in 25 ml of benzene is added dropwise within 30 minutes. The reaction mixture heats up to 38°. It is stirred for 2 hours at room temperature; to the reaction mixture is then added a further 2.5 g of potassium tert.-butoxide and it is subsequently stirred for 15 hours at room temperature. The cloudy reaction mixture is filtered clear with the aid of diatomaceous earth; it is concentrated by evaporation and the evaporation residue is chromatographed on a silica-gel column with an ethyl acetate/hexane mixture (volume ratio 1:1). There is obtained 2-methyl-2-(2-pyrrolidinylidene)-acetophenone, m.p. 91°-92° (from cyclohexane).

b. By the process described in Example 1 there is obtained, from 32.5 g of 2-methyl-2-(2-pyrrolidinylidene)-acetophenone and 33.3 g of triethyloxonium-tetrafluoroborate, crude 2-(1-methyl-2-ethoxy-2-phenyl-ethenyl)-1-pyrroline-tetrafluoroborate. This is a viscous oil which can be reacted with cyclohexylamine without further purification.

EXAMPLE 28

5 g (0.025 mole) of N-(α-methylbenzylidene)-cyclohexylamine, 5.6 g (0.05 mole) of 2-ethoxy-pyrroline and 2.4 g (0.025 mole) of methanesulphonic acid are heated together for 2 hours at 100° with stirring. The reaction mixture is then cooled, diluted with ethyl acetate and, after commencing crystallisation cooled with ice. The formed salt is filtered off and recrystallised from isopropanol/ether to obtain 2-[2-(cyclohexylimino)-2-phenyl-ethylidene]-pyrrolidine-methanesulphonate-(1:1), m.p. 186°-187°.

The N-(α-methylbenzylidene)-cyclohexylamine used as starting material is produced as follows:

12 g (0.1 mole) of acetophenone and 12 g (0.12 mole) of cyclohexylamine are dissolved in 200 ml of toluene. 0.1 g of p-toluenesulphonic acid is added, and the solution is refluxed for 15 hours, with the reaction water being separated by means of a water separator. The toluene is subsequently evaporated off in the rotary evaporator, and the residue is distilled under high vacuum, whereupon N-(α-methylbenzylidene)-cyclohexylamine passes over at 99°-101°/0.001 mm Hg.

What we claim is:

1. A compound of the formula I

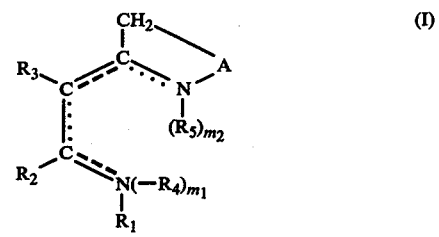

wherein
$R_1$ represents an aliphatic or cycloaliphatic hydrocarbon radical having a maximum of 12 carbon atoms, phenyl which is unsubstituted or substituted by lower alkyl, lower alkoxy, halogen up to atomic number 35 and/or trifluoromethyl, or phenyl-lower alkyl or diphenyl-lower alkyl, which radicals are unsubstituted or substituted in the phenyl ring(s) as hereinbefore indicated for phenyl,
$R_2$ represents phenyl which is unsubstituted or substituted by lower alkyl, lower alkoxy, halogen up to atomic number 35 and/or trifluoromethyl,
$R_3$ represents hydrogen or lower alkyl,
$R_4$ represents, if present, lower alkyl,
$R_5$ represents, if present, hydrogen or lower alkyl,
A represents ethylene, and
$m_1$ and $m_2$ represent 0 or 1 and together always represent 1, and wherein two additional bonds, either corresponding to the dashed lines or corresponding to the dotted lines, are present, with $m_1$ representing 0 in the former case and $m_2$ representing 0 in the latter case, and its acid addition salts.

2. A compound according to claim 1 having the formula I, wherein $R_1$ represents an aliphatic hydrocarbon having a maximum of 8 carbon atoms, or a cycloaliphatic hydrocarbon radical having a maximum of 12 carbon atoms, $R_2$ represents phenyl which is unsubstituted or substituted by lower alkyl, lower alkoxy, halogen up to atomic number 35 and/or trifluoromethyl, $R_3$ represents hydrogen, $R_4$, if present, represents lower alkyl, $R_5$, if present, represents hydrogen or lower alkyl, and A, $m_1$ and $m_2$ have the meanings given in claim 1 and its pharmaceutically acceptable acid addition salts.

3. A compound according to claim 1 having the formula I, wherein $R_1$ represents an aliphatic hydrocarbon radical which has a maximum of 8 carbon atoms or a cycloaliphatic hydrocarbon radical which has a maximum of 12 carbon atoms, $R_2$ represents phenyl which is unsubstituted or substituted by methyl, methoxy or halogen up to atomic number 35, $R_3$ represents hydrogen, $R_4$, if present, represents lower alkyl, $R_5$, if present, represents hydrogen or lower alkyl and A, $m_1$ and $m_2$ have the meanings given in claim 1, and its pharmaceutically acceptable acid addition salts.

4. A compound according to claim 1 having the formula I, wherein $R_1$ represents a saturated aliphatic hydrocarbon radical which has a maximum of 8 carbon atoms, or a saturated cycloaliphatic hydrocarbon radical having 5 to 12 carbon atoms, $R_2$ represents phenyl which is unsubstituted or substituted by methyl, methoxy or halogen up to atomic number 35, $R_3$ represents hydrogen, $R_4$, if present, represents lower alkyl $R_5$, if present, represents hydrogen or lower alkyl and A, $m_1$ and $m_2$ have the meanings given in claim 1 and its pharmaceutically acceptable acid addition salts.

5. A compound according to claim 1 having the formula I, wherein $R_1$ represents a saturated aliphatic hydrocarbon radical which has a maximum of 8 carbon atoms and which is bound by way of a secondary or tertiary carbon atom, or a saturated cycloaliphatic hydrocarbon radical having 5 to 12 carbon atoms, $R_2$ represents phenyl which is unsubstituted or substituted by methyl, methoxy or halogen up to atomic number 35, $R_3$ represents hydrogen, $R_4$, if present, represents lower alkyl, $R_5$, if present, represents hydrogen or lower alkyl and A, $m_1$ and $m_2$ have the meanings given in claim 1, and its pharmaceutically acceptable acid addition salts.

6. A compound according to claim 1 which is 2-[2-(cyclohexyl-imino)-2-phenyl-ethylidene]-pyrrolidine, and its pharmaceutically acceptable acid addition salts.

7. A compound according to claim 1 which is 2-[2-(cis-2-cyclohexyl-cyclopentylimino)-2-phenylethylene]-pyrrolidine, and its pharmaceutically acceptable acid addition salts.

8. A pharmaceutical composition for the oral treatment of hyperglycaemia in mammals comprising a hypoglycaemically effective amount of a compound according to claim 1 and having the formula I

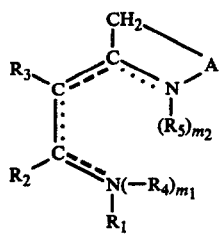

wherein
$R_1$ represents an aliphatic or cycloaliphatic hydrocarbon radical having a maximum of 12 carbon atoms, phenyl which is unsubstituted or substituted by lower alkyl, lower alkoxy, halogen up to atomic number 35 and/or trifluoromethyl, or phenyl-lower alkyl or diphenyl-lower alkyl, which radicals are unsubstituted or substituted in the phenyl ring(s) as hereinbefore indicated for phenyl,
$R_2$ represents phenyl which is unsubstituted or substituted by lower alkyl, lower alkoxy, halogen up to atomic number 35 and/or trifluoromethyl,
$R_3$ represents hydrogen or lower alkyl,
$R_4$ represents, if present, lower alkyl,
$R_5$ represents, if present, hydrogen or lower alkyl,
A represents ethylene, and
$m_1$ and $m_2$ represent 0 or 1 and together always represent 1, and wherein two additional bonds, either corresponding to the dashed lines or corresponding to the dotted lines, are present, with $m_1$ representing 0 in the former case and $m_2$ representing 0 in the latter case, or of a pharmaceutically acceptable acid addition salt of a compound of formula I, and a pharmaceutical carrier substance.

9. A pharmaceutical composition according to claim 8, wherein a hypoglycaemically effective amount of a compound of formula I given in claim 8, wherein $R_1$ represents an aliphatic hydrocarbon having a maximum of 8 carbon atoms, or a cycloaliphatic hydrocarbon radical having a maximum of 12 carbon atoms, $R_2$ represents phenyl which is unsubstituted or substituted by lower alkyl, lower alkoxy, halogen up to atomic number 35 and/or trifluoromethyl, $R_3$ represents hydrogen, $R_4$, if present, represents lower alkyl, $R_5$, if present, represents hydrogen or lower alkyl, and A, $m_1$ and $m_2$ have the meanings given in claim 8, or of a pharmaceutically acceptable acid addition salt thereof is present.

10. A pharmaceutical composition according to claim 8, wherein a hypoglycaemically effective amount of a compound of formula I given in claim 8, wherein $R_1$ represents a saturated aliphatic hydrocarbon radical which has a maximum of 8 carbon atoms, or a saturated cycloaliphatic hydrocarbon radical having 5 to 12 carbon atoms, $R_2$ represents phenyl which is unsubstituted or substituted by methyl, methoxy or halogen up to atomic number 35, $R_3$ represents hydrogen, $R_4$, if present, represents lower alkyl, $R_5$, if present, represents hydrogen or lower alkyl and A, $m_1$ and $m_2$ have the meanings given in claim 8, or of a pharmaceutically acceptable acid addition salt thereof is present.

11. A pharmaceutical composition according to claim 8, wherein a hypoglycaemically effective amount of 2-[2-(cyclohexyl-imino)-2-phenyl-ethylidene]-pyrrolidine or of a pharmaceutically acceptable acid addition salt thereof is present.

12. A pharmaceutical composition according to claim 8, wherein a hypoglycaemically effective amount of 2-[2-(cis-2-cyclohexyl-cyclopentylimino)-2-phenylethylene]-pyrrolidine or of a pharmaceutically acceptable acid addition salt thereof is present.

13. A method for the treatment of hyperglycaemia in a mammal comprising oral administration to said mammal of a hypoglycaemically effective amount of a compound according to claim 1 having the formula I defined in claim 1, or of a pharmaceutically acceptable acid addition salt thereof.

14. A method according to claim 13 comprising oral administration of a hypoglycaemically effective amount of 2-[2-cyclohexyl-imino)-2-phenyl-ethylidene]-pyrrolidine or of a pharmaceutically acceptable acid addition salt thereof.

15. A method according to claim 13 comprising oral administration of a hypoglycaemically effective amount of 2-[2-(cis-2-cyclohexyl-cyclopentylimino)-2-phenyl-ethylidene]-pyrrolidine or of a pharmaceutically acceptable acid addition salt thereof.

* * * * *